United States Patent
Steinemann et al.

(10) Patent No.: US 6,656,490 B1
(45) Date of Patent: Dec. 2, 2003

(54) OPTHALMOLOGIC USES OF PROTEIN C

(75) Inventors: Thomas L. Steinemann, Little Rock, AR (US); Ivory A. Reis, Little Rock, AR (US); Louis M. Fink, Little Rock, AR (US); Harry H. Brown, Little Rock, AR (US); Richard A. Marlar, Denver, CO (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 1826 days.

(21) Appl. No.: 08/596,698

(22) Filed: Feb. 5, 1996

Related U.S. Application Data

(63) Continuation of application No. 08/237,649, filed on May 4, 1994, now abandoned.

(51) Int. Cl.$^7$ .............................. A61F 2/00; A61K 38/00
(52) U.S. Cl. ............................ 424/427; 424/428; 514/2; 514/21
(58) Field of Search ......................... 424/427, 422–426; 514/2, 21

(56) References Cited

U.S. PATENT DOCUMENTS

| | | | | |
|---|---|---|---|---|
| 4,849,403 A | * | 7/1989 | Stocker | 514/2 |
| 5,084,273 A | * | 1/1992 | Hirahara | 424/94.6 |
| 5,147,638 A | * | 9/1992 | Esmon | 426/85.8 |
| 5,151,268 A | * | 9/1992 | Bang | 424/94.64 |

OTHER PUBLICATIONS

Iverson et al., Arch. Opthalmol., 109:405 (1991).
Howard et al., Arch Opthalmol., 109:272 (1991).
Snyder et al., Arch. Opthalmol., 105:1277 (1987).
Johnson et al., Opthalmol., 95:312 (1988).

* cited by examiner

*Primary Examiner*—Gollamudi S. Kishore
(74) *Attorney, Agent, or Firm*—Benjamin Aaron Adler

(57) ABSTRACT

The present invention provides a method of reducing intraocular fibrin comprising the administration of a pharmacologically effective dose of Protein C to an individual having elevated levels of intraocular fibrin. Also provided are various methods of preventing intraocular fibrin formation, treating intraocular diseases and reducing intraocular inflammation.

21 Claims, 9 Drawing Sheets

(N=4)

OPTHALMOLOGIC USES OF PROTEIN C

This is a continuation of application Ser. No. 08/237,649 filed on May 4, 1994, now abandoned.

BACKGROUND OF THE INVENTION

1. Field of the Invention

The present invention relates generally to the fields of opthalmology, ocular pharmacology and protein chemistry. More specifically, the present invention relates to novel opthalmologic uses of Protein C.

2. Description of the Related Art

Formation of intraocular fibrin subsequent to ocular surgery, inflammation, hemorrhage or trauma is a serious medical problem. Fibrin deposition can also occur in diabetic eye disease, uveitis and vitreoretinopathy and can severely compromise the outcome of glaucoma filtering or vitreoretinal surgery.

Uveitis is an inflammation of any structure of the uveal tract, which includes the iris, ciliary body or choroid. Anterior uveitis results in a breakdown of the blood-aqueous barrier with concentration of protein in the aqueous that can increase up to a hundred fold compared to the normal state. During inflammation, white blood cells, plasma proteins and inflammatory mediators from blood vessels in the iris and ciliary body are released into the aqueous humor. Activation of the clotting cascade results in fibrin formation in the anterior chamber with detrimental effects on vision.

The possible causes for postoperative fibrinous membrane formation include preexisting vascular incompetance, (e.g., severe diabetes mellitus) uveitis due to surgical trauma, reactions to the intraocular implants and their coating material or infections subsequent to surgery. Regardless, the exact pathogenesis of the postoperative, and other, fibrin responses remains unknown.

The management of severe postoperative fibrin response by current means is often ineffective. Generally, treatment is oriented toward reduction of postoperative inflammation and attempted reestablishment of the blood-ocular barrier using topical or systemically administered corticosteroids. Unfortunately, corticosteroid use is often ineffective and, moreover, can cause complications in patients with diabetes mellitis or glaucoma.

Heparin has been used to reduce fibrin formation but leads to increased bleeding. More recently, attempts have been made to treat ocular fibrin depostion using tissue plasminogen activator. Recombinant human tPA injected intraoccularly has been effective but its use is complicated by increased incidence of intraocular hemorrhage. Moreover, at doses above 25 micrograms, tPA is toxic to the retina. The use of tPA to treat hyphema, a post-traumatic collection of blood in the anterior chamber of the eye, has also been examined with questionable clinical benefits.

The prior art is deficient in the lack of effective means of inhibiting the depostion of fibrin caused by a variety of pathophysiological states. The present invention fulfills this longstanding need and desire in the art.

SUMMARY OF THE INVENTION

In one embodiment of the present invention, there is provided a method of reducing intraocular fibrin comprising the administration of a pharmacologically effective dose of Protein C to an individual having elevated levels of intraocular fibrin.

In another embodiment of the present invention, there is provided a method of preventing intraocular fibrin formation comprising the administration of a pharmacologically effective dose of Protein C to an individual at risk for development of elevated levels of intraocular fibrin.

In yet another embodiment of the present invention, there is provided a method of treating intraocular disease comprising the administration of a pharmacologically effective dose of Protein C to an individual having said disease, said individual being at risk for development of elevated levels of intraocular fibrin.

In another embodiment of the present invention, there is provided a method of reducing ocular inflammation comprising the administration of a pharmacologically effective dose of Protein C to an individual having said ocular inflammation.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
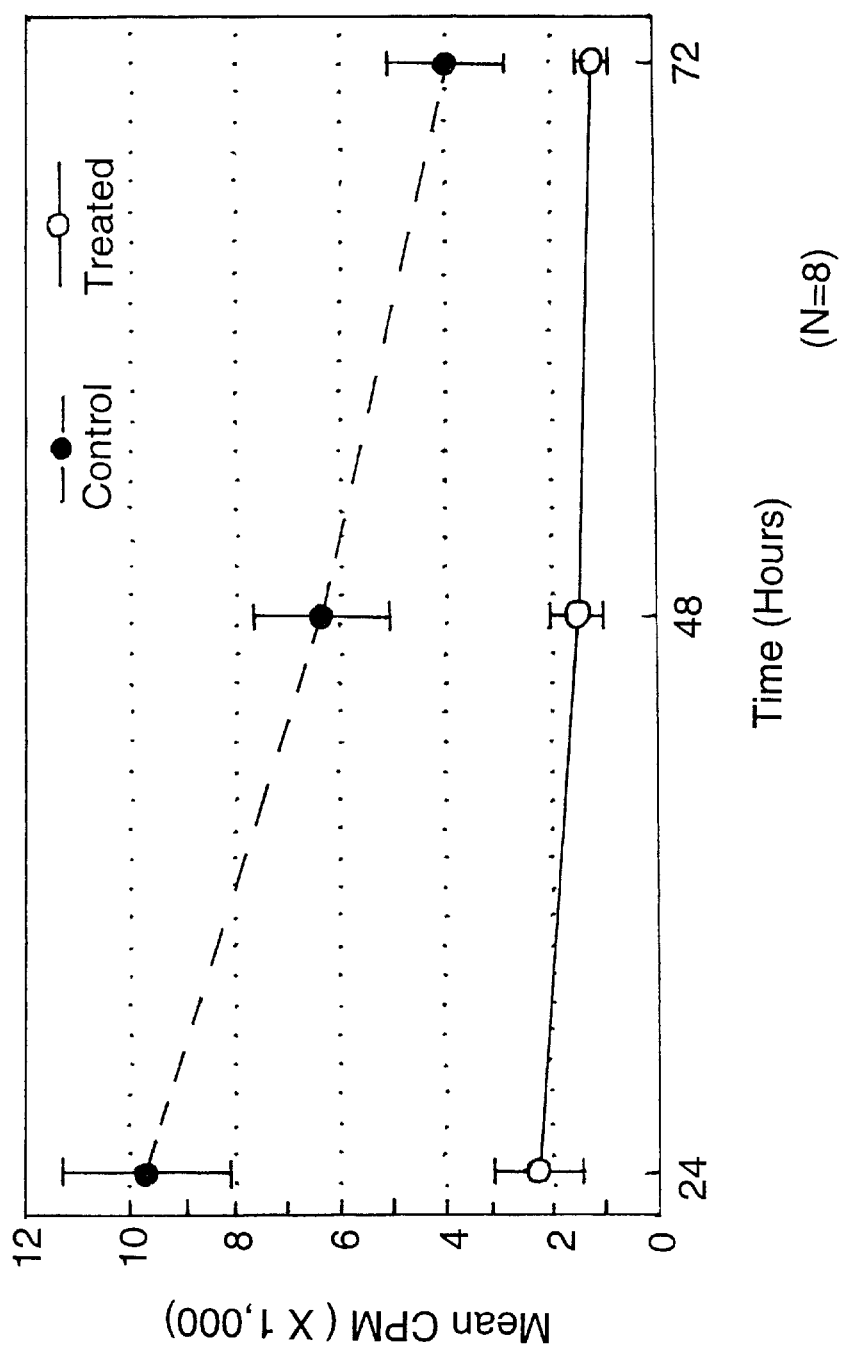
FIG. 1 shows the effect of Protein C on $^{125}$I-fibrin over a seventy-two hour time period. There is a significant reduction in fibrin in treated versus control eyes in all time periods as measured by radioactive counts emitted from $^{125}$I-fibrin.
Figure 2:
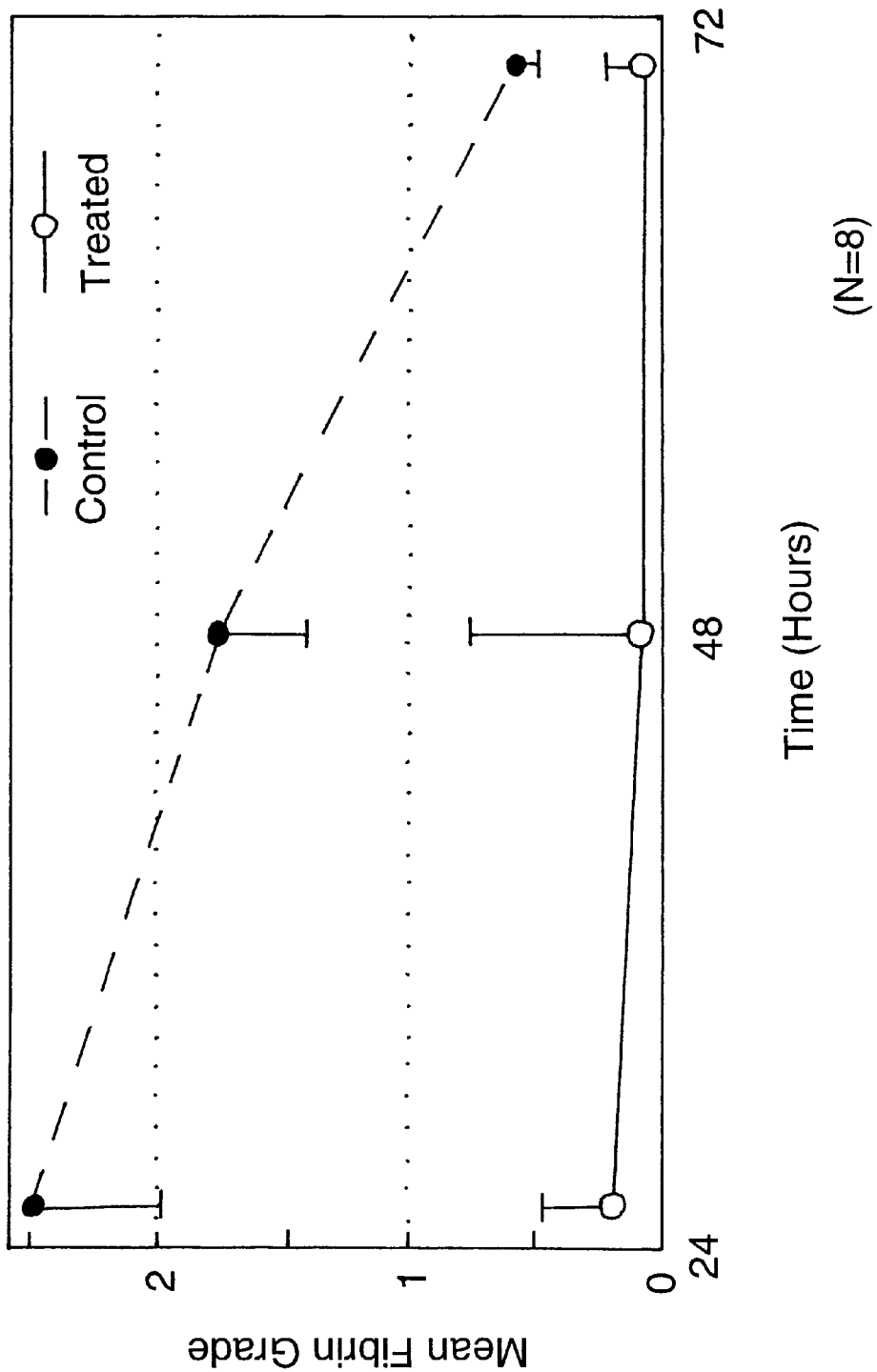
FIG. 2 shows the effect of Protein C on qualitative fibrin grade over a seventy-two hour time period. The mean fibrin grade is significantly lower for treated eyes compared to controls.
Figure 3:
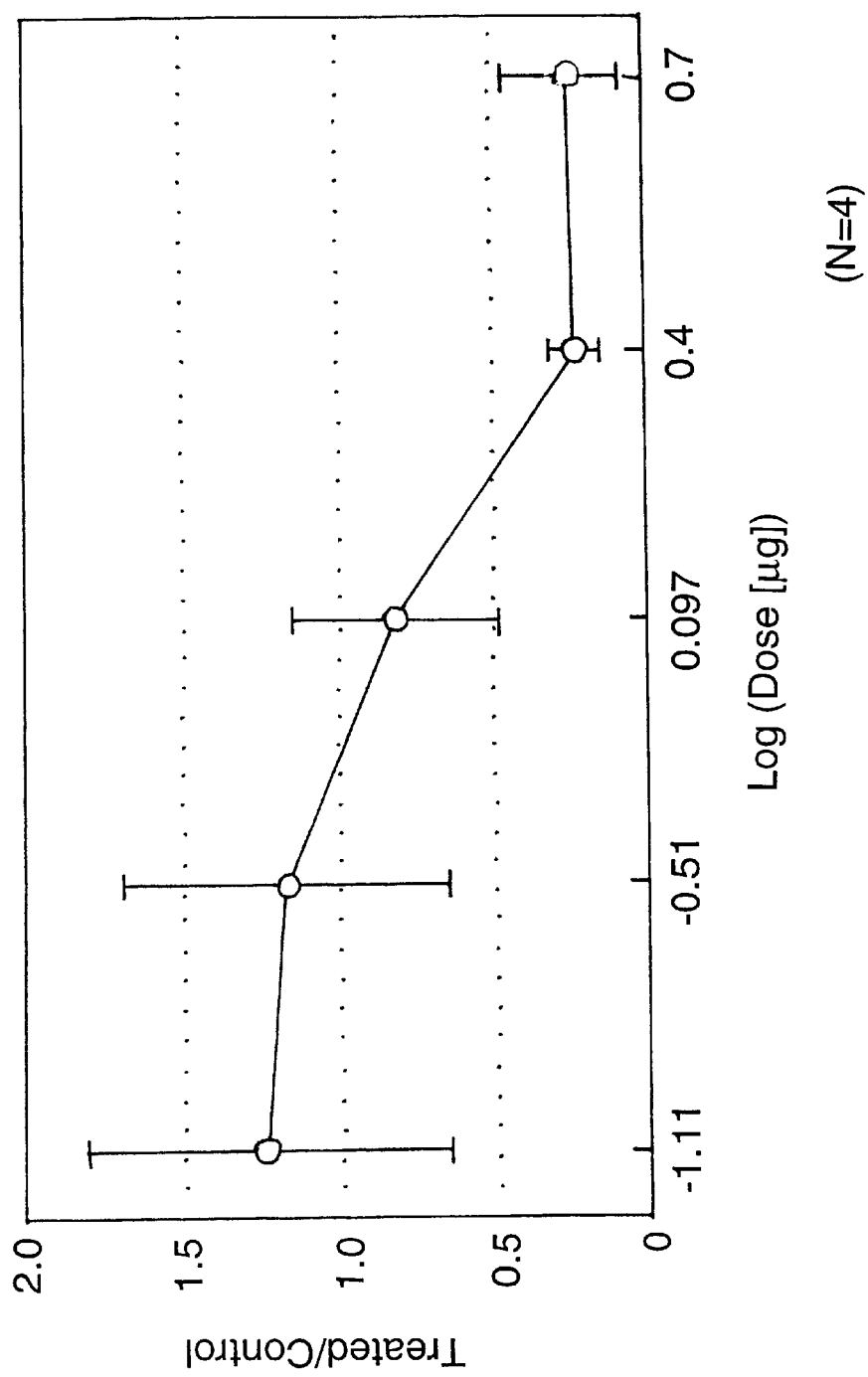
FIG. 3 shows the effect of various concentrations of Protein C on $^{125}$I-fibrin per minute at 24 hours post injection. A linear reduction in $^{125}$I-fibrin is noted with higher concentrations.
Figure 4:
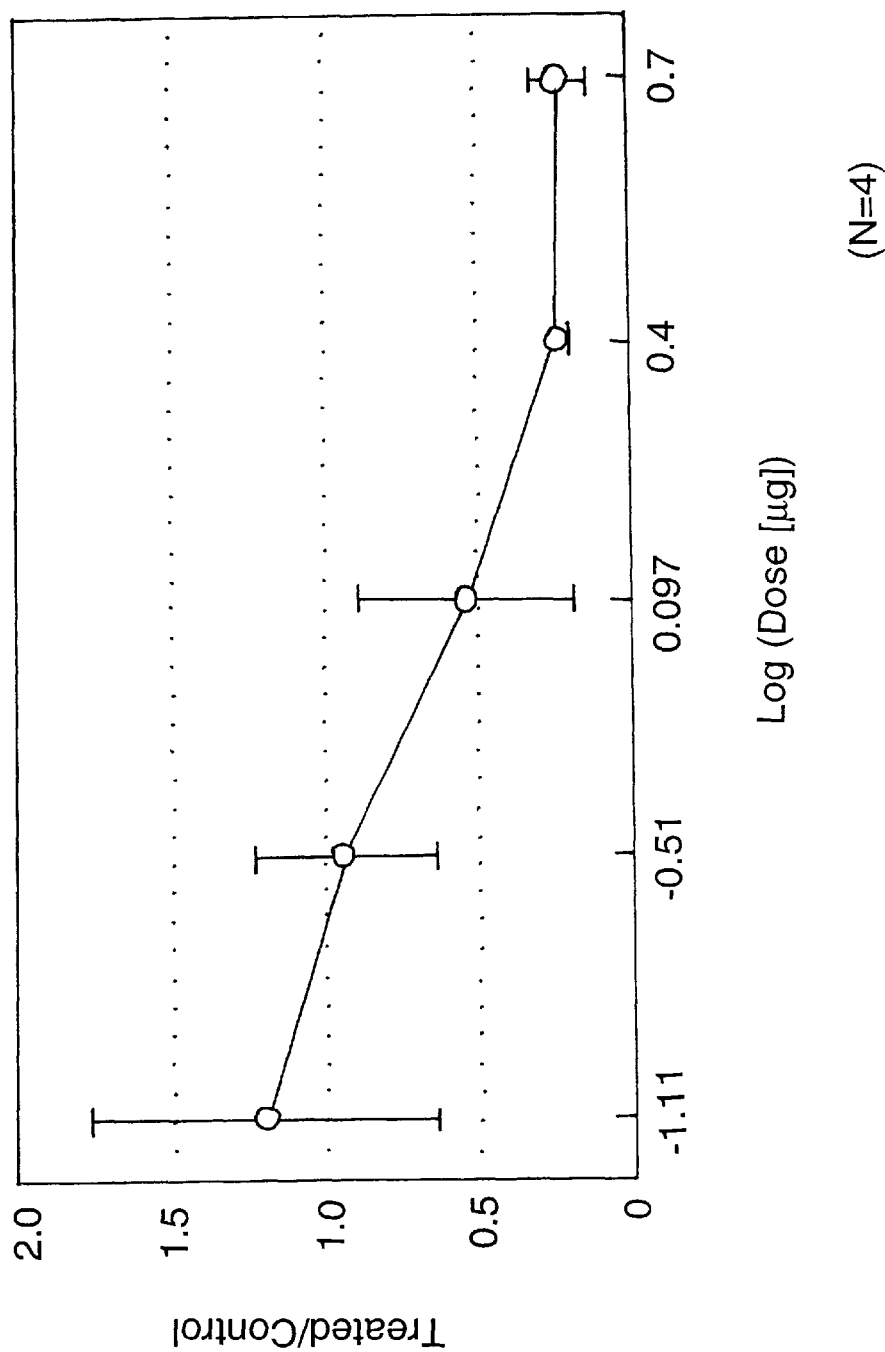
FIG. 4 shows a dose response curve demonstrating various concentrations of Protein C on $^{125}$I-fibrin per minute at 48 hours. A linear reduction in $^{125}$I-fibrin is noted with higher concentrations.
Figure 5:
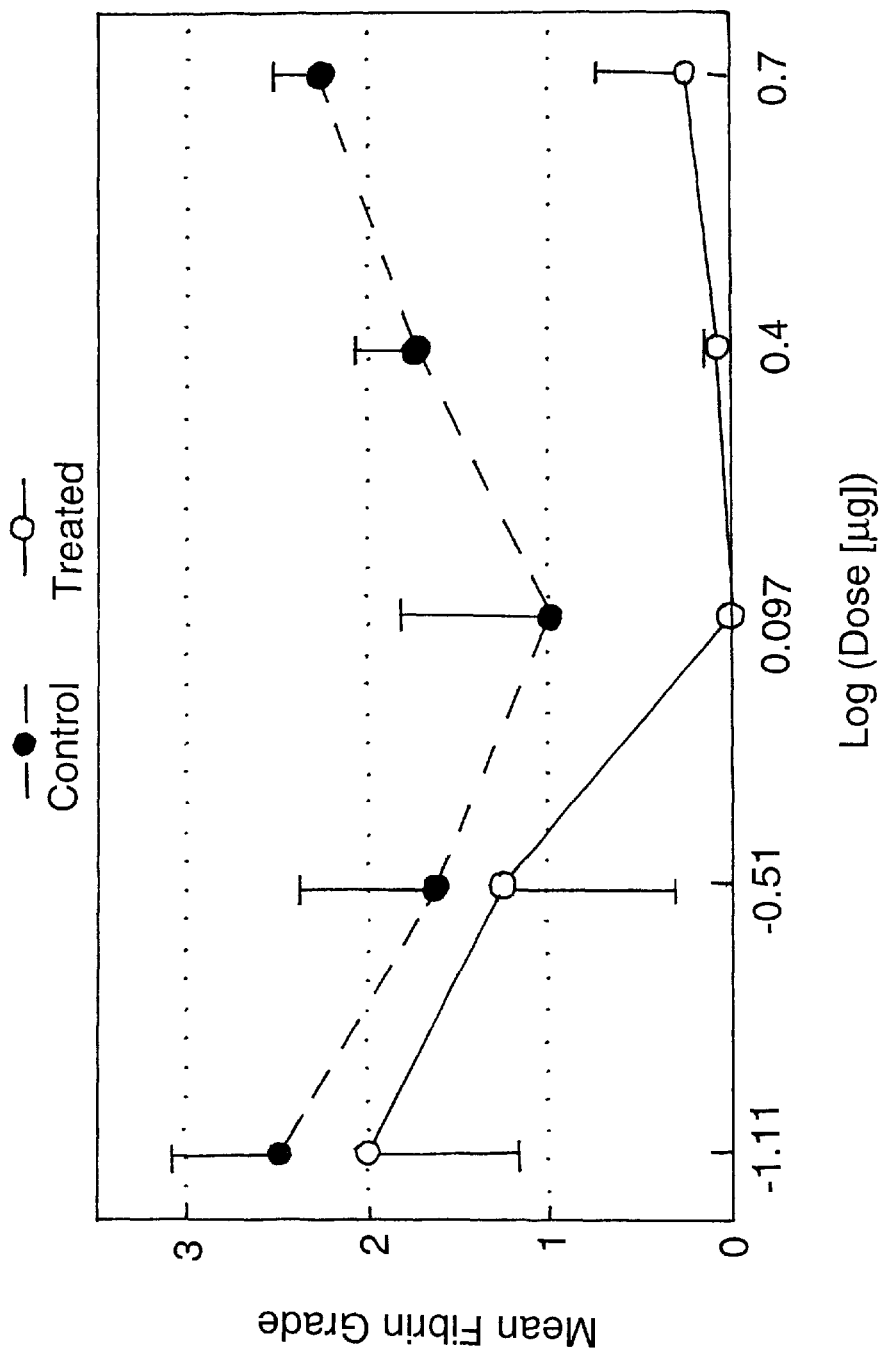
FIG. 5 shows the effects of various concentrations of Protein C on qualitative fibrin grade after 48 hours. A significant difference between treatment and control eyes is seen at dosages at 2.5 ug per eye (log dose=0.4) and higher.
Figure 6:
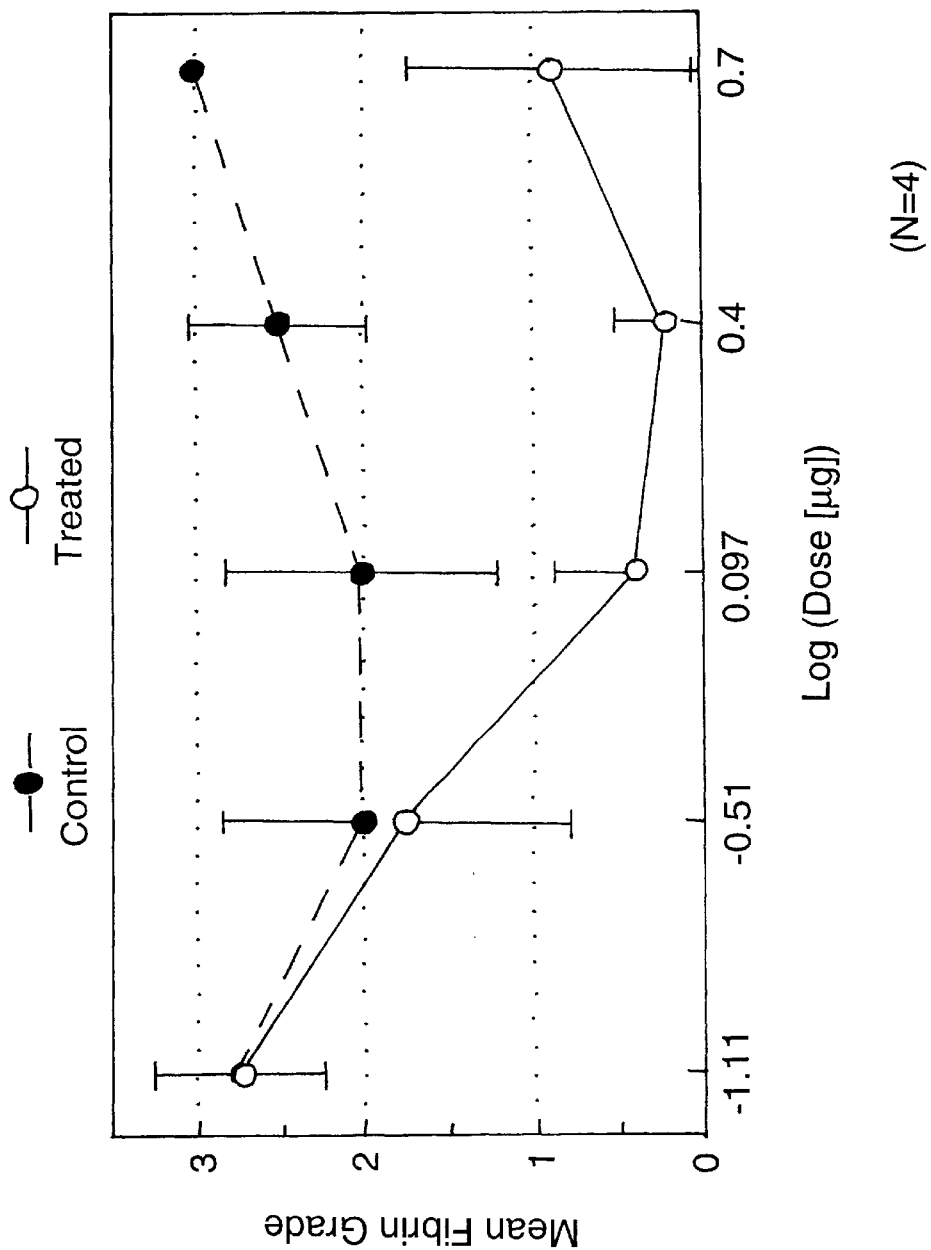
FIG. 6 shows the effects of various concentrations of Protein C on qualitative fibrin grade after 24 hours. A significant difference between treatment and control eyes is seen at dosages of 1.25 ug per eye (log dose=0.097) and higher.

The present invention provides a method of reducing intraocular fibrin comprising the administration of a pharmacologically effective dose of Protein C to an individual having elevated levels of intraocular fibrin. Generally, any form of protein C will be useful in the methods of the present invention. For example, Protein C may be selected from the group consisting of human Protein C and activated Protein C. The human Protein C and activated Protein C may be obtained from pooled human sera. Recombinant human Protein C may also be used in the methods of the present invention. In addition, protein S may be co-administered with protein C in any of the methods disclosed by the present invention.

Generally, the dose of the protein C-type compound in the methods of the present invention is that dose which effectively reduces or prevents the formation of intraocular fibrin in the particular physiological state in which intraocular fibrin formation is considered to be deleterious. More specifically, the Protein C is preferably administered in a concentration of from about 1.0 micrograms per milliliter to about 25.0 micrograms per milliliter. When co-administered with protein C, the concentration of protein S is from about 10.0 micrograms per milliliter to about 100.0 micrograms per milliliter.

Generally, the route of administration of the protein C-type compound in the methods of the present invention is that route which effectively reduces or prevents the formation of intraocular fibrin in that particular physiological state in which intraocular fibrin formation is considered to be deleterious. More specifically, the route of administration of Protein C is selected from the group consisting of topical, including applying the drug to a contact lens (collagen shield) administration, intracameral, intravitreal or subconjunctival injection. A person having ordinary skill in this art would readily recognize the benefits of one particular route of administration over another in the methods of the present invention.

The methods of the present invention may be varied by the practictioner in this art to maximize the reduction of intracocular fibrin. For example, the administration of the Protein C-type compound in the methods of the present invention may be concurrent with intraocular surgery. Thus, the protein C-type compounds would be administered concurrently with various intraocular surgeries such as cataract surgery, vitrectomy, gluacoma filtering procedure, corneal transplantation and proliferative vitreoretinopathy.

The present invention is also directed to a method of preventing intraocular fibrin formation comprising the administration of a pharmacologically effective dose of Protein C to an individual at risk for development of elevated levels of intraocular fibrin.

In another embodiment, the present invention is directed to a method of treating intraocular disease comprising the administration of a pharmacologically effective dose of Protein C to an individual having said disease, said individual being at risk for development of elevated levels of intraocular fibrin. Representative examples of intraocular disease is selected from the group consisting of uveitis, severe diabetes mellitis, anterior segment inflammatory states, post-traumatic states, (e.g., hyphema, intravitreal bleeding and subretinal hemorrhaging) retinopathy of prematurity and proliferative vitreoretinopathy.

The present invention also encompasses a method of reducing ocular inflammation comprising the administration of a pharmacologically effective dose of Protein C to an individual having said ocular inflammation. Representative examples of ocular inflammatory states include uveitis, including or patients with inflammatory glaucoma, immediate post-operative or post-traumatic states, i.e., patients who have undergone glaucoma filtration surgery or in patients who have had corneal transplant surgery.

Fibrin forms in the eye in various eye diseases and causes severe visual loss. Protein C and protein S are vitamin K-dependent plasma proteins that modulate coagulation via the protein C anticoagulant pathway. The protein C anticoagulant pathway regulates blood coagulation by the proteolytic inactivation of factors Va and VIIIa. The present invention shows that protein C and protein S injected intraocularly will reduce fibrin formation in the eye. The present invention also shows protein C alone reduces fibrin formation.

The present invention demonstrates that activated protein C inhibits fibrin formation in the eye. Administration of protein C resulted in no signs of toxicity and no increased risk of hemorrhage. Thus, the present invention illustrates a major improvement in the prophylactic treatment for intraocular fibrin.

The following examples are given for the purpose of illustrating various embodiments of the invention and are not meant to limit the present invention in any fashion.

EXAMPLE 1

Protein C and Protein S in Aqueous Humor

Protein C and Protein S were measured by established methods in the art. Assays of 4 rabbit and 10 human aqueous samples showed no Protein C or Protein S. Aqueous humor was withdrawn from normal human eyes during cataract surgery. It was expected that non-inflamed eyes would have no Protein C or Protein S. No detectable Protein C or Protein S was observed.

EXAMPLE 2

Fibrin Formation in Rabbit

Formation of fibrin was induced in rabbit eyes by injection of 0.2 ml of rabbit plasma or 0.2 ml of human plasma into the anterior chamber essentially as described by Snyder et al., *Arch. Ophthalmol.*, 105:1277–1280 (1987). Briefly, following systemic and topical anesthesia, a paracentesis was performed with a 30 gauge needle and 0.2 ml of aqueous humor was replaced with 0.2 ml of the rabbit or human plasma. A fibrin clot generally forms rapidly, usually within three hours. The utility of the rabbit uveitis model with regard to correlating effects of drugs observed in this model with corresponding disease states in humans can be readily discerned by those with ordinary skill in this art through references such as Snyder et al., (cited above), Johnson et al., Ophthalmology, 95:5920596 (1988), and Iverson et al., Arch Ophthalmol 109:405–409 (1991).

EXAMPLE 3

Effect of Protein C on Fibrin Formation in Rabbit Uveitis Model

The present invention demonstrates that the mixture of Protein C and Protein S decreases fibrin formation in the eye as graded on a scale of (0–3+) in a masked manner. Using the rabbit uveitis model, fibrin formation in the eye was induced by injection of rabbit plasma. Experimental eyes were given intraocular injection of activated Protein C (2.5 µg) while control eyes were injected with an equal volume of balanced salt solution (BSS). Masked examinations assessed fibrin quantity (0–3+) and measured gamma radiation (counts/minute). Fibrin was quantified on a scale of 0–3+:

0=No fibrin

1+=Iris details

2+=Blurring of iris details

3+=Iris details obscured

Figure 7:
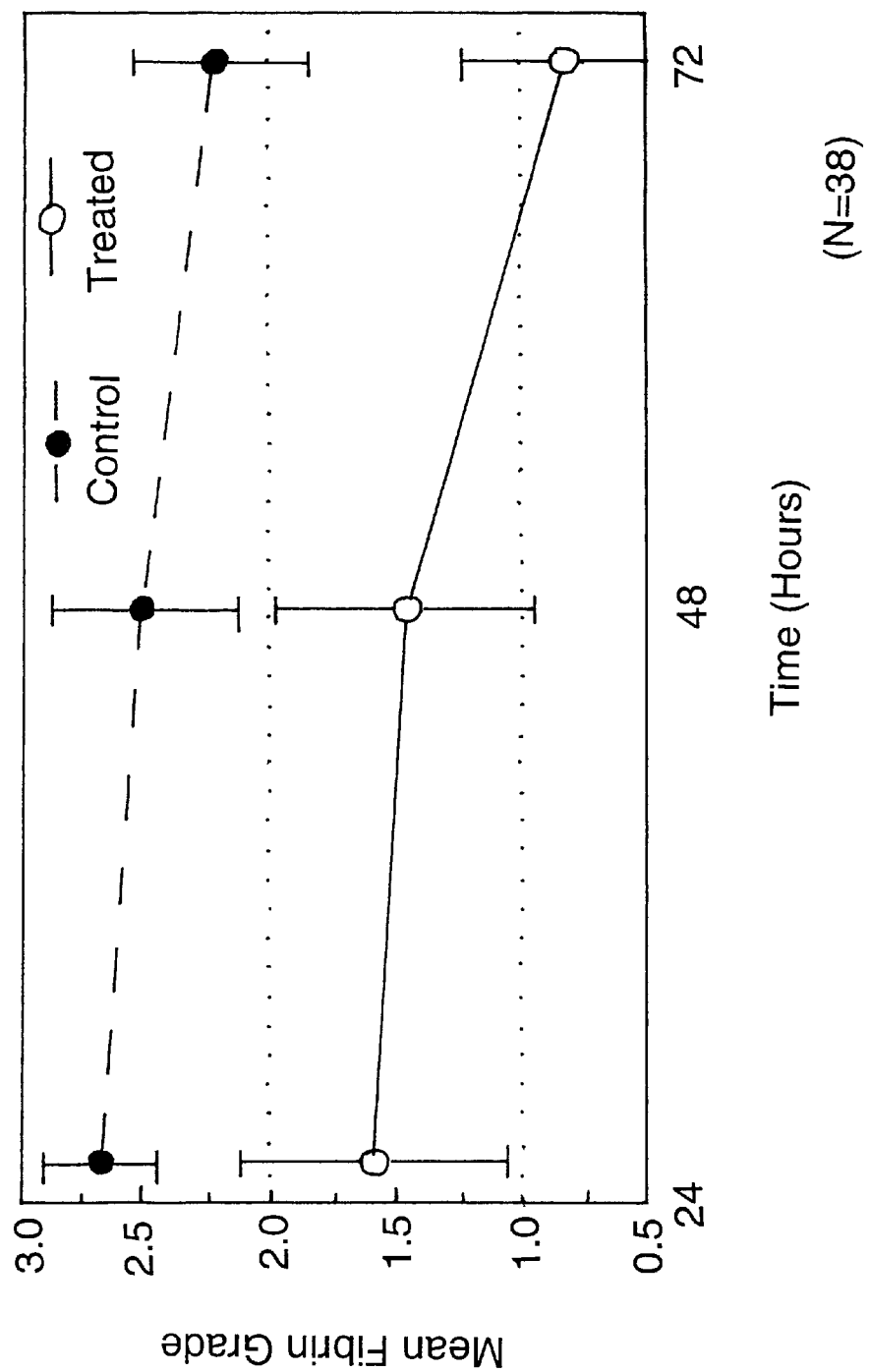
FIG. 7 shows the effects of Protein C (0.1 ug/eye) and Protein S (1.0 ug/eye) on qualitative fibrin grade measured every 24 hours for 72 hours. A significant reduction in treated eyes is noted for all time periods.

A dose response curve was then produced using 4-fold dilutions of protein C. TABLE I and FIG. 7 show that in 6 rabbits (one eye of each treated, the other control) the average fibrin in the anterior chamber at 24, 48 and 72 hours was as follows:

TABLE I

| | Fibrin in Anterior Chamber | | | | | |
|---|---|---|---|---|---|---|
| | 24 hours | | 48 hours | | 72 hours | |
| Rabbit | tx | control | tx | control | tx | control |
| 3029 | 0 | 1.5 | 0 | 1.5 | 0 | 0.5 |
| 3030 | 0 | 3 | 0 | 3 | 0 | 3 |
| 3031 | 3 | 3 | 2.5 | 2.5 | 1 | 1.5 |
| 3032 | 0 | 3 | 0 | 2.5 | 0 | 2.5 |
| 3033 | 3 | 3 | 3 | 3 | 1 | 3 |
| 3034 | 3 | 2 | 3 | 0.5 | 1.5 | 1.5 |
| Total | 9 | 15.5 | 8.5 | 13 | 3.5 | 12 |
| Mean | 1.5 | 2.6 | 1.3 | 2.2 | 0.6 | 2.0 |

Microscopic analysis revealed inflammation in 4/6 control eyes and 1/6 treated eyes. No signs of retinal toxicity were noted.

EXAMPLE 4

Quantitative Model for Fibrin and Protein C

Using $^{125}$I-fibrinogen, radioactivity was measured in a mature fibrin clot using a gamma counter held in front of the rabbit's eye at a fixed distance. Differences in radioactive counts between treated (Protein C) and control eyes (balanced salt solution) were statistically significant in 16 rabbits. Radioactivity counts were taken immediately after injection and every 24 hours for 72 hours. Animals were sacrificed and the eyes were prepared for histologic section. Autoradioagraphy was used to localize the radioactivity in the histologic sections. Decreased amounts of radioactive fibrinogen-fibrin complexes were observed in treated eyes. In addition, there was a good correlation with the qualitative fibrin clot grading using the method described above.

EXAMPLE 5

Figure 8:
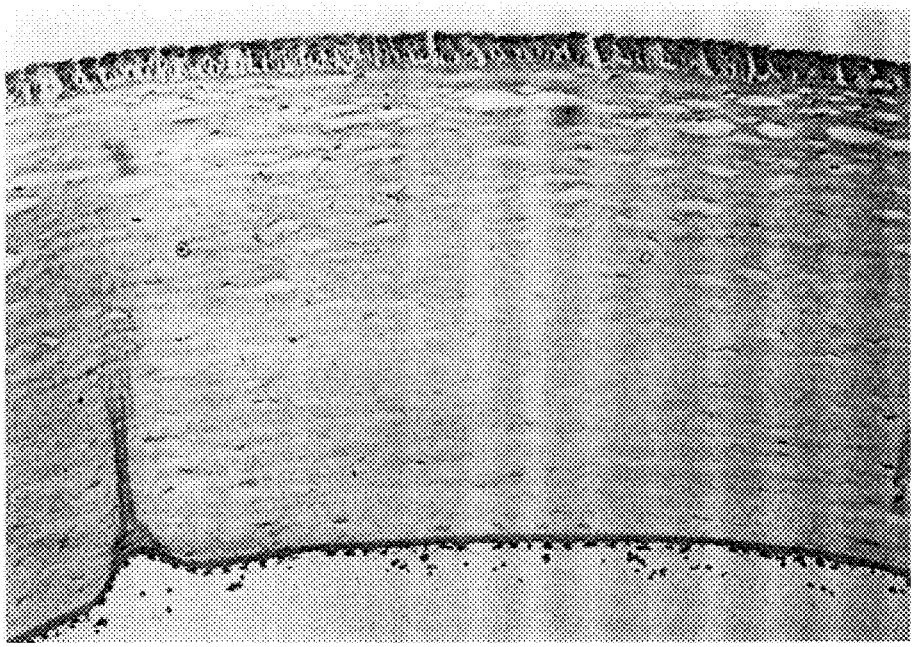
FIG. 8 shows a photomicrograph of a rabbit cornea in an animal treated with Protein C. No signs of toxicity are evident.
Figure 9:
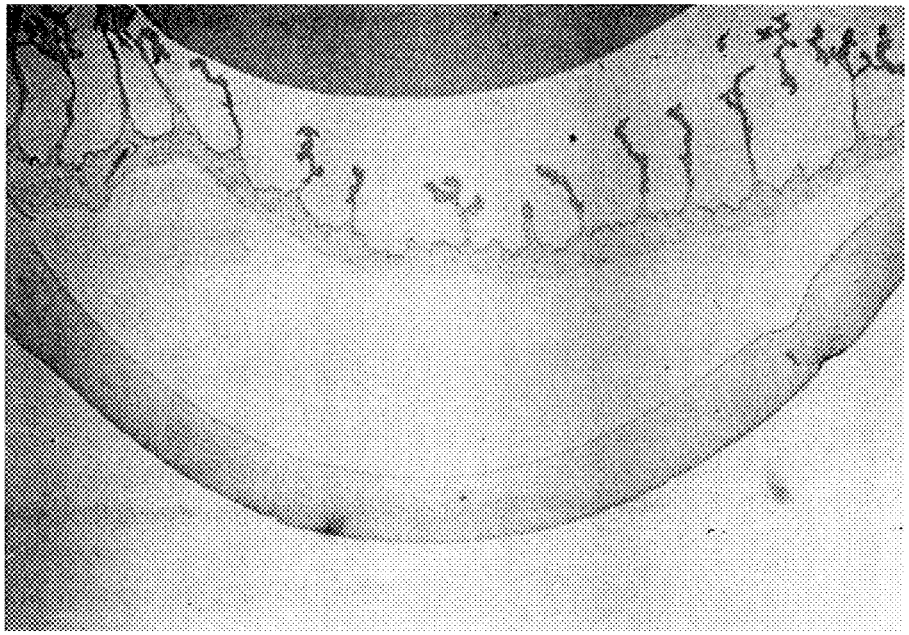
FIG. 9 shows a photomicrograph of an anterior segment of a rabbit eye in an animal treated with Protein C including the cornea, anterior chamber, ciliary body and lens. No signs of toxicity are evident.
Figure 10:
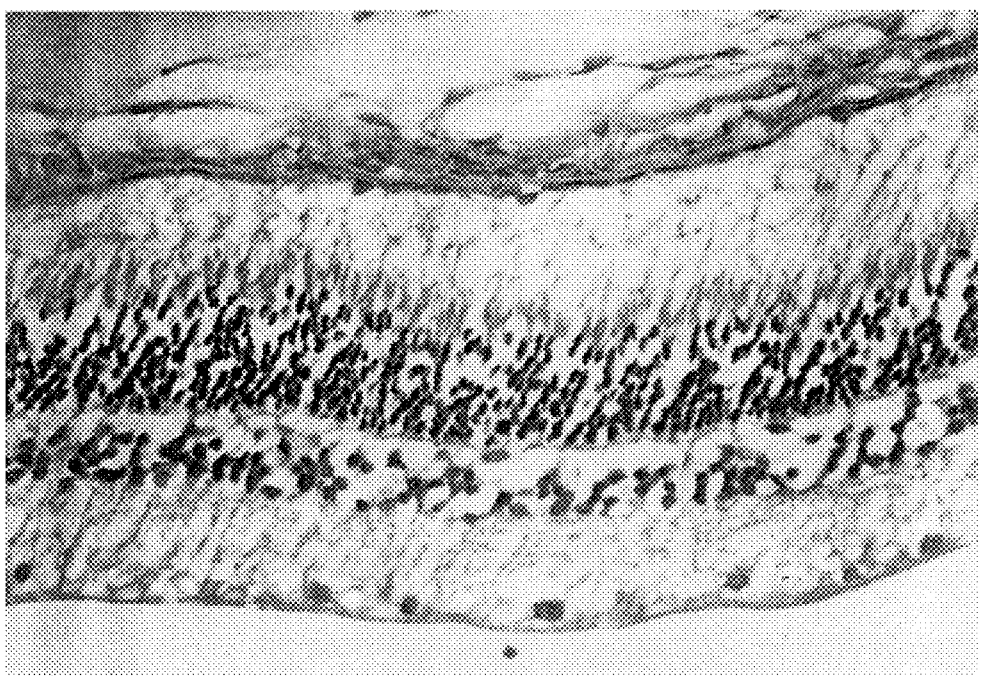
FIG. 10 shows a photomicrograph of the retina of a rabbit eye treated with Protein C. No signs of toxicity are evident.

All invasive procedures were preceded by topical administration of proparacaine (0.5%), intramuscular xylazine (5 mg/kg) and ketamine hydrochloride (35 mg/kg). First, a 30 gauge needle paracentesis was performed and 0.2 ml of aqueous humor fluid was withdrawn from each eye of 25 adult New Zealand white rabbits. Subsequently, 0.2 ml of rabbit plasma was injected into the anterior chamber of each eye. Using this method of fibrin formation, clots form within three hours and cross-linked fibrin clots form within 24 hours. Experimental eyes were injected with activated recombinant human Protein C and human plasma Protein S in a series of concentrations from 1–10 micrograms. Control eyes were injected with an equivalent volume of a Balanced Salt Solution. Eyes were followed for 72 hours and the amount of fibrin in the anterior chamber was graded on a scale of 0–3+. Slit lamp photographs of several eyes were taken. After 72 hours, the animals were sacrificed with 3 cc of pentobarbital injected into a marginal ear vein. The eyes were enucleated and prepared for light microscopy. FIG. 8 shows a photomicrograph of a rabbit cornea in an animal treated with Protein C. FIG. 9 shows a photomicrograph of an anterior segment of a rabbit eye in an animal treated with Protein C including the cornea, anterior chamber, ciliary body and lens. FIG. 10 shows a photomicrograph of the retina of a rabbit eye treated with Protein C. No signs of toxicity were evident in any of the tissue examined histologically.

EXAMPLE 6

Quantitation of Intraocular Fibrin

Intraocular fibrin is quantitated by two different methods. First, a fibrin clot is measured in each eye using a digitalized photographic technique. Using this technique with plasma and protein C or protein S or a Balanced Salt Solution control, fibrin clots are formed in each eye. Slit lamp photographs are then taken of each eye and the resulting kodachrome slide are analyzed using a camera that digitalizes the area of the clot within the photograph. Areas of fibrin clot are then calculated and compared for treatment versus control animals.

Secondly, the amount of opacity within the anterior chamber which is proportional to the size and density of the fibrin clot is measured using a light opacity meter. Ten New Zealand white rabbits are used. A fibrin optic light is shown directly into the animal's eyes. All stray and reflective light produced from the fibrin clot is detected by the light opacity meter. This allows quantification and comparisons between treated and control eyes. Measurements are taken immediately at 6 hours and every 12 hours for 72 hours post-injection. As discussed previously, topical analgesia consisting of proparacaine hydrochloride (0.5%) is used prior to anterior chamber paracentesis. In addition, the animals are given an intramuscular injection of xylazine (5 mg/kg) and ketamine hydrochloride (35 mg/kg) prior to any intraocular injections. Post-anesthetic monitoring is as described above.

EXAMPLE 7

The present invention also encompasses the use of Protein C to improve retinal survival when retinal damages occurs in the aftermath of subretinal hemorrhage. For example, Protein C would be useful in patients with subretinal neovascular membrane bleeding, such as found in individuals with age-related macular degeneration, or in patients after retinal trauma. In these case Protein C would be injected into retinal hemorrhages and clots soon after formation.

The use of Protein C to improve retinal survival is illustrated by the following example. Subretinal macular hemorrhages are created using a Nd:YAG laser focused on pre-formed retinal blebs. Using a pars plana vitrectomy approach, a 20–33 gauge glass micropipette is used to infuse Protein C into the subretinal space for about 2–12 minutes at a rate of about 5 to about 20 microliters per minute. The total dose ranges form about 0.31 micrograms to about 2.5 micrograms. A one hour perior allows for fibrin prophylaxis and fibrinolysis. The clot is then evacuated using a glass micropipette connected to suction at a rate of 97 to 200 microliters per minute. The animals are sacrificed and enucleated and treated. Control eyes are prepared for histology to assess the retinal architecture. Retinal section photomicrographs are graded in a masked fashion by an opthalmic pathologist.

EXAMPLE 8

The present invention also encompasses the use of Protein C to reduce inflammatory states in the eye, i.e., decreasing conjunctival and iris vascular engorgement and anterior chamber cell and flare. This anti-inflammatory effect of Protein C is useful in such opthalmic conditions as immediate post-operative or post-traumatic states or in those patients who have undergone glaucoma filtration surgery, in patients with inflammatory glaucoma or to reduce the risk of corneal transplant rejection.

The anti-inflammatory effects of Protein C are shown in a standard rabbit eye model for iridocyclitis. In this model, bacterial enterotoxin or lippolysaccharide (LPS) is injected intravenously in rabbits daily for 5–7 days creating a standard model of human uveitis. One eye is treated with Protein C; the other eye receives a control treatment of BSS. The amount of anterior chamber cell and flare is qualitatively graded and recorded in a masked fashion using a slit lamp camera. Aqueous humor is assayed in each eye for inflammatory cells and mediators such as interleukins, cytokines and arachidonic acid metabolites are measured. Subtle breakdown of the blood aqueous barrier (which reflects inflammatory mediator release) is quantified using fluorophotometry. The salutary effects on preservation of healthy corneal transplants and viable glaucoma filtration surgery is tested by performing these surgeries and then subjecting the eyes to the above treatment and observing for graft or filter failure using the slit lamp and observing the tissues histologically following animal sacrifice.

EXAMPLE 9

It is also specifically contemplated that Protein C could be used in conjunction with tissue plasminogen activator inhibitor to modulate the production and elimination of fibrin in corneal wounding. Protein C prevents fibrin formation and plasminogen activator inhibitor blocks the release of plasmin. Thus, the use together of Protein C and plasminogen activator inhibitor would modulate the early stages of corneal wound healing and thus minimize early tissue repair mechanisms. This use of Protein C is illustrated by the following example.

Rabbits are given a lamellar keratectomy bilaterally. One eye receives a combination of Protein C and plasminogen activator inhibitor while the other eye receives BSS as a control. After epithelial wound healing, the animals are sacrificed immediately and at weekly intervals for four weeks. Prior to sacrifice, animals are examined at the slit lamp and the amount of corneal stromal haze is graded in a masked fashion. Following sacrifice, the eyes are enucleated and examined histologically by a masked observer grading the amount of new collagen.

Any publications mentioned in this specification are indicative of the levels of those skilled in the art to which the invention pertains. All publications mentioned are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of reducing amounts of intraocular fibrin comprising the administration of a pharmacologically effective dose of Protein C so as to reduce the amount of intraocular fibrin in an individual having elevated levels of intraocular fibrin.

2. The method of claim 1, wherein said Protein C is selected from the group consisting of human Protein C and activated Protein C.

3. The method of claim 1, wherein said Protein C is administered in a concentration of from about 1.0 micrograms per milliliter to about 25.0 micrograms per milliliter.

4. The method of claim 1, wherein said administration of Protein C is selected from the group consisting of topical administration, subconjunctival injection, intracameral injection and intravitreal injection.

5. The method of claim 1, wherein said administration is concurrent with intraocular surgery.

6. The method of claim 5, wherein said intraocular surgery is selected from the group consisting of cataract surgery, vitrectomy, gluacoma filtering procedure, corneal transplantation and surgery for proliferative vitreoretinopathy.

7. The method of claim 1, further comprising the co-administration of a pharmacologically effective dose of Protein S to an individual having elevated levels of intraocular fibrin.

8. The method of claim 7, wherein said Protein S is administered in a concentration of from about 10.0 micrograms per milliliter to about 100.0 micrograms per milliliter.

9. A method of inhibiting intraocular fibrin formation comprising the administration of a pharmacologically effective dose of Protein C so as to reduce the amount of intraocular fibrin in an individual at risk for development of elevated levels of intraocular fibrin.

10. The method of claim 9, wherein said Protein C is selected from the group consisting of human Protein C and activated Protein C.

11. The method of claim 10, wherein said Protein C is administered in a concentration of from about 1.0 micrograms per milliliter to about 10.0 micrograms per milliliter.

12. The method of claim 9, wherein said administration of Protein C is selected from the group consisting of topical administration, subconjunctival injection, intracameral injection and intravitreal injection.

13. A method of treating intraocular disease comprising the administration of a pharmacologically effective dose of Protein C so as to reduce the amount of intraocular fibrin in an individual having said disease, said individual being at risk for development of elevated levels of intraocular fibrin.

14. The method of claim 13, wherein said Protein C is selected from the group consisting of human Protein C and activated Protein C.

15. The method of claim 13, wherein said Protein C is administered in a concentration of from about 1.0 micrograms per milliliter to about 25.0 micrograms per milliliter.

16. The method of claim 9, wherein said administration of Protein C is selected from the group consisting of topical administration, subconjunctival injection, intracameral injection and intravitreal injection.

17. The method of claim 16, wherein said intraocular disease is selected from the group consisting of uveitis, end-stage diabetes mellitis, anterior segment inflammatory states, post-traumatic states and retinopathy of prematurity.

18. The method of claim 9, wherein said administration is concurrent with intraocular surgery.

19. The method of claim 18, wherein said intraocular surgery is selected from the group consisting of cataract surgery, vitrectomy, gluacoma filtering procedure, corneal transplantation and surgery for proliferative vitreoretinopathy.

20. The method of claim 9, further comprising the co-administration of a pharmacologically effective dose of Protein S to an individual having elevated levels of intraocular fibrin.

21. The method of claim 20, wherein said Protein S is administered in a concentration of from about 10.0 micrograms per milliliter to about 100.0 micrograms per milliliter.

* * * * *

UNITED STATES PATENT AND TRADEMARK OFFICE
CERTIFICATE OF CORRECTION

PATENT NO. : 6,656,490 B1
DATED : December 2, 2003
INVENTOR(S) : Thomas L. Steinemann et al.

It is certified that error appears in the above-identified patent and that said Letters Patent is hereby corrected as shown below:

<u>Title page, Item [54] and Column 1, line 1,</u>
Title, "OPTHALMOLOGIC" should read -- OPHTHALMOLOGIC --.

<u>Column 1</u>
Line 9, "opthalmology" should read -- ophthalmology --.
Line 11, "opthalmologic" should read -- ophthalmologic --.

<u>Column 7,</u>
Lines 5 and 12, "opthalmic" should read -- ophthalmologic --.

Signed and Sealed this

Twenty-fourth Day of February, 2004

JON W. DUDAS
*Acting Director of the United States Patent and Trademark Office*